US012357516B2

(12) United States Patent
Ye

(10) Patent No.: US 12,357,516 B2
(45) Date of Patent: Jul. 15, 2025

(54) ABSORBENT CORE COMPRISING A HIGH LOFT CENTRAL LAYER AND TWO DIFFERENT SUPERABSORBENT POLYMERS

(71) Applicant: The Procter & Gamble Company, Cincinnati, OH (US)

(72) Inventor: Fengchun Ye, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 248 days.

(21) Appl. No.: 17/542,592

(22) Filed: Dec. 6, 2021

(65) Prior Publication Data

US 2023/0172770 A1 Jun. 8, 2023

(30) Foreign Application Priority Data

Dec. 10, 2020 (WO) ............... PCT/CN2020/135174

(51) Int. Cl.
*A61F 13/534* (2006.01)
*A61F 13/15* (2006.01)
*A61F 13/551* (2006.01)
*A61F 13/53* (2006.01)

(52) U.S. Cl.
CPC ...... *A61F 13/534* (2013.01); *A61F 13/15699* (2013.01); *A61F 13/55105* (2013.01); *A61F 2013/15406* (2013.01); *A61F 2013/15471* (2013.01); *A61F 2013/1556* (2013.01); *A61F 2013/530554* (2013.01); *A61F 2013/53445* (2013.01)

(58) Field of Classification Search
CPC ............. A61F 13/534; A61F 13/15699; A61F 2013/15406; A61F 2013/15471; A61F 2013/1556; A61F 2013/530554; A61F 2013/53445; A61F 13/15617; A61F 2013/530481
See application file for complete search history.

(56) References Cited

U.S. PATENT DOCUMENTS

| | | | | |
|---|---|---|---|---|
| 2012/0308780 | A1* | 12/2012 | Rottger | ................. A61F 13/534 156/499 |
| 2016/0175169 | A1* | 6/2016 | Bianchi | ............... A61F 13/5323 604/385.101 |
| 2017/0095380 | A1* | 4/2017 | Wirtz | ...................... A61L 15/60 |
| 2022/0192899 | A1* | 6/2022 | Lee | .................... B01J 20/28004 |

FOREIGN PATENT DOCUMENTS

| CN | 108024886 A | 5/2018 |
|---|---|---|
| WO | 2020025401 A1 | 2/2020 |

OTHER PUBLICATIONS

PCT Search Report and Written Opinion for PCT/CN2020/135174 dated Jan. 6, 2021, 13 pages.

* cited by examiner

*Primary Examiner* — Susan S Su
*Assistant Examiner* — Erin A Kim
(74) *Attorney, Agent, or Firm* — Daniel S. Albrecht

(57) ABSTRACT

An absorbent core for use in an absorbent article including a high loft central layer having deposited on two different surfaces thereon a first superabsorbent polymer SAP1 and a second superabsorbent polymer SAP2 in the form of particles that are at least partially distributed within the high loft layer. The SAP1 has a higher capacity than SAP2 and the permeability of SAP2 is more than 5×10-7 cm3·s/g.

20 Claims, 8 Drawing Sheets

ABSORBENT CORE COMPRISING A HIGH LOFT CENTRAL LAYER AND TWO DIFFERENT SUPERABSORBENT POLYMERS

FIELD OF THE INVENTION

The invention relates to absorbent cores and their use in personal hygiene absorbent articles. The absorbent cores may be in particular used in baby diapers.

BACKGROUND OF THE INVENTION

Absorbent articles for personal hygiene such as disposable baby diapers, training pants for toddlers or adult incontinence undergarments, are designed to absorb and contain body exudates, in particular urine. These absorbent articles comprise several layers providing different functions, typically including a topsheet, a backsheet and an absorbent core in-between, among other layers.

The absorbent core should be able to absorb and retain the exudates for a prolonged amount of time, for example overnight for a diaper, minimize re-wet to keep the wearer dry, and avoid soiling of clothes or bed sheets. Absorbent cores have typically comprised a blend of comminuted wood pulp cellulose fibers with superabsorbent polymers (SAP) particles, also called absorbent gelling materials (AGM), as absorbent material.

Absorbent cores without fluff cellulose fibers (also called "airfelt-free" cores) have been more recently proposed. The SAP particles may be for example enclosed within discrete pockets formed between two substrates (see e.g. WO95/11654, Tanzer et al.). It has also been proposed to immobilize SAP particles with a microfibrous adhesive network to a nonwoven substrate by an adhesive (see e.g. WO2008/155699A1, Hundorf et al.).

More recently, airfelt-free cores have been disclosed comprising a high loft, fibrous, central layer with SAP at least partially distributed within this high loft layer (see e.g. WO2016/106,021A1, Bianchi et al.). SAP particles are applied on each side of the high loft nonwoven, with the SAP particles deposited on the surface of the high loft layer being at least partially distributed and immobilized within the pores of the high loft layer. A tissue paper or a nonwoven is further adhesively attached on each of the high loft central layer to further immobilize the particles within the high loft central layer. At least the top cover layer which is planned to be oriented towards the topsheet on the absorbent article should be fluid-pervious. A further wrap layer may be typically used to further stabilize these layers and form the absorbent core. These absorbent cores are typically continuously produced as a unitary stream that can be collected in a roll. The roll can be transported to a diaper manufacturing line, where the absorbent cores are individualized by cutting and continuously assembled with the other components of the absorbent articles.

Disclosures of this type of absorbent cores include WO2020/025401 (BASF, Ge et al.), WO2020/032280, WO2020/032281, WO2020/032282, WO2020/032283 and WO2020/032284 (Nippon SHOKUBAI). It has been proposed to use different types of SAP on the top side and bottom side of the high loft layer respectively: a high permeability SAP in the top side layer and a high retention capacity SAP in the bottom side layer.

There is a continuous need to improve the performances of absorbent cores, in particular in terms of absorption speed, capacity, low rewet and wearer comfort, while keeping the overall costs of manufacture as low as possible.

SUMMARY OF THE INVENTION

The present invention is directed to an absorbent core extending in a transversal direction and a longitudinal direction, having a thickness in a vertical direction, and which comprises a liquid-permeable top cover layer, a bottom cover layer, and a central layer sandwiched between the top cover layer and the bottom cover layer. The central layer is a high loft porous layer, such as a carded nonwoven, having a top surface oriented toward the top cover layer and a bottom surface oriented towards the bottom cover layer. The absorbent core comprises two different types of superabsorbent polymer (SAP) particles deposited on the respective side of the high loft core, and which are at least partially distributed within the central layer. According to the invention, the absorbent core comprises:

a first superabsorbent polymer ("SAP1") in the form of particles deposited on the top surface of the high loft central layer;

a second superabsorbent polymer ("SAP2") in the form of particles deposited on the bottom surface of the high loft central layer.

While it has been suggested in the past to deposit a high permeability SAP on the top side, and a high retention capacity SAP on the bottom surface of the high loft layer, the present invention has found that when the first SAP has a higher capacity than the second SAP, as measured by the CRC method, and the second SAP has a permeability of more than 5 UPM units, as measured by the UPM method, then an absorbent core having overall good balance between acquisition speed and rewet is obtained. Preferably, SAP2 has a higher permeability than SAP1.

The absorbent core may comprise at least 60% by weight of SAP (all combined), in particular at least 70% by weight, relative to the total weight of the core. The high loft central layer may be formed entirely from synthetic fibers, and may be substantially free of fluff cellulose fibers, although natural or natural-sourced fibers such a cellulose or cotton fibers or viscose fibers may also be present in the central layer and/or the top cover layer and/or the bottom cover layer.

The top cover layer and the bottom cover layer may typically be a nonwoven or a tissue paper. Low basis weight tissue paper for example is readily available and a relatively cheap substrate. The absorbent core may also comprise a wrapping layer that completely covers the bottom cover layer or top cover layer, typically forming a C-wrap around the longitudinally extending side edges of these layers and thus better immobilize the SAP particles within the absorbent core. A wrapping layer can provide an improved containment of the SAP thus preventing losses on the side edges of the core. Alternatively, such a C-wrap may also be formed by the top cover layer or the bottom cover layer.

The absorbent cores may also comprise a dual high loft layer construction comprising a first central high loft layer and a second central high loft layer. This construction may provide additional benefit for example in terms of SAP immobilization and a higher quantity of SAP particles may be distributed within two layers. These and other optional features of the invention will be described in the following description.

DETAILED DESCRIPTION OF THE INVENTION

Introduction

Figure 1:
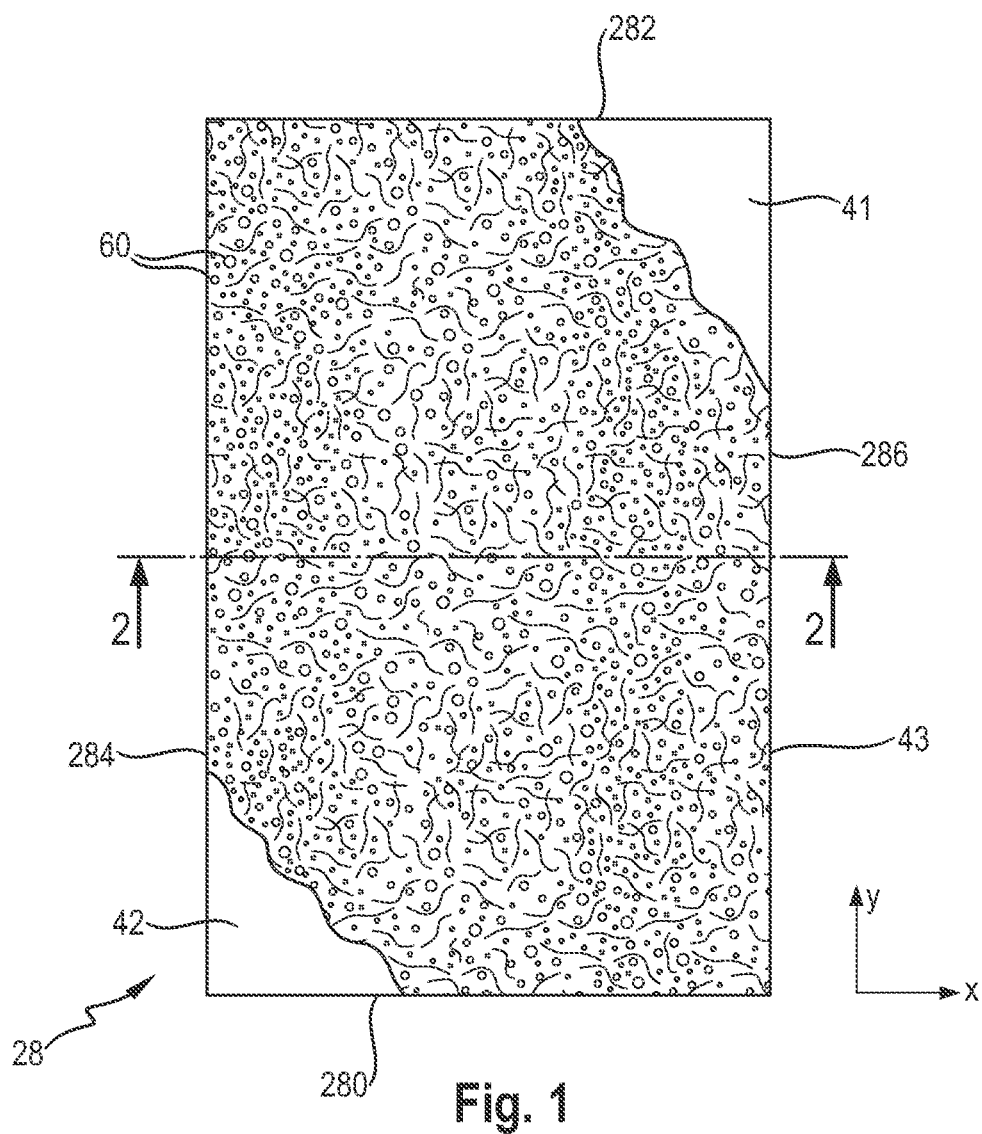
FIG. 1 shows a top view of an exemplary absorbent core with the top and central layers partially removed.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

As used herein, the terms "nonwoven", nonwoven layer" or "nonwoven web" are used interchangeably to mean an engineered fibrous assembly, primarily planar, which has been given a designed level of structural integrity by physical and/or chemical means, excluding weaving, knitting or papermaking (ISO 9092:2019 definition). The directionally or randomly orientated fibers, are bonded by friction, and/or cohesion and/or adhesion. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yarn). Nonwoven webs can be formed by many processes such as meltblowing, spunbonding, solvent spinning, electrospinning, carding and airlaying. The basis weight of nonwoven webs is usually expressed in grams per square meter (g/m2 or gsm).

General Description of the Absorbent Core

As used herein, the term "absorbent core" refers to a component for an absorbent article comprising an absorbent material that can absorb and retain body fluid, in particular urine. The absorbent cores according to this invention are typically manufactured in a continuous stream that can be stored and transported for example as a roll of absorbent core material, and are then individualized when integrated in an absorbent article, such as a diaper. Absorbent cores have the most absorbent capacity of the components of the absorbent article and comprises all, or at least the majority of, superabsorbent polymer (herein referred to as "SAP") particles. The terms "absorbent core" and "core" are herein used interchangeably. Some absorbent products may comprise two or more distinct absorbent cores but typically there is only one absorbent core in an absorbent product such as a diaper.

The absorbent cores of the invention are substantially planar. By substantially planar, it is meant that the absorbent core can be laid flat on a planar surface and primarily extend in an x and an y direction. The absorbent cores may also be typically thin and conformable, so that they can also be laid on a curved surface for example a drum during the making process, or stored and handled as a continuous roll of stock material comprising a plurality of cores before being converted into an absorbent article.

An exemplarily individualized absorbent core is represented in a flat state of FIG. 1. The absorbent core's height in the z direction is small relative to its other dimensions in the transversal direction x and the longitudinal direction y. Unless otherwise indicated, dimensions and areas disclosed herein apply to the core in this flat-out configuration.

For ease of discussion, the absorbent cores, articles and processes of the invention will be discussed with reference to the Figures and the numerals referred to in these Figures; however these are not intended to limit the scope of the claims unless specifically indicated.

High Loft Central Layer 43

Figure 2:
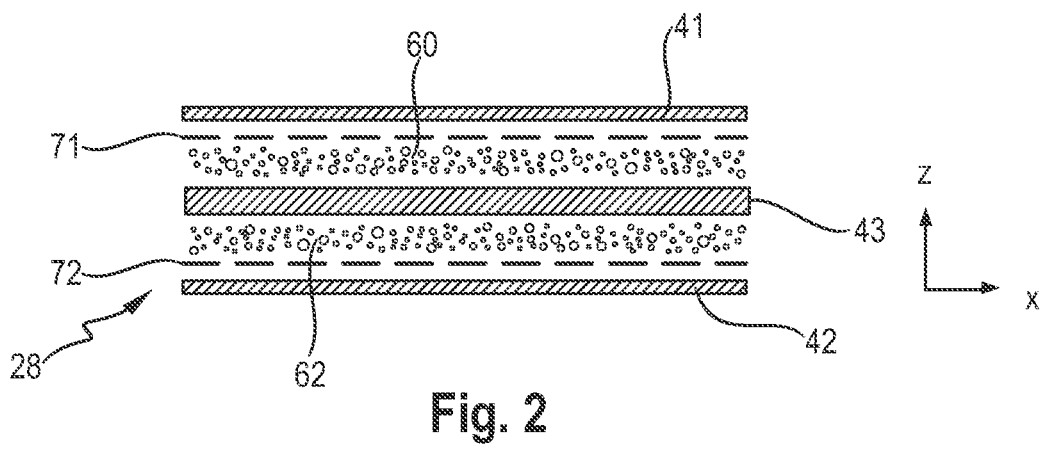
FIG. 2 shows a schematic exploded cross-sectional view of an absorbent core.

The absorbent cores of the invention comprise a high loft central layer 43, as first illustrated in FIGS. 1-2. The term "high loft" refers to low density bulky fabrics, as compared to flat, paper-like fabrics. High loft webs are characterized by a relatively high porosity. This means that there is a relatively high amount of void space in which superabsorbent polymer particles can be distributed.

The high loft layer (without the superabsorbent particles) of the invention may have a density at a pressure of 4.14 kPa (0.6 psi) below 0.20 g/cm$^3$, in particular ranging from 0.05 g/cm$^3$ to 0.15 g/cm$^3$.

The high loft layer (without the superabsorbent particles) of the invention may have a density at a pressure of 2.07 kPa (0.3 psi) below 0.20 g/cm$^3$, in particular ranging from 0.02 g/cm$^3$ to 0.15 g/cm$^3$.

The high loft layer (without the superabsorbent particles) of the invention may have a density at a pressure of 0.83 kPa (0.12 psi) below 0.15 g/cm$^3$, in particular ranging from 0.01 g/cm$^3$ to 0.15 g/cm$^3$.

The density can be calculated by dividing the basis weight of the high loft layer by its thickness measured at the respective pressure as indicated (see the method details further below in the "test procedure" section).

The central layer is preferably a nonwoven, but other types of high loft material are not excluded. The central layer may comprise or consist of synthetic fibers, optionally mixed with natural fibers such as cellulose or cotton fibers or viscose fibers for example. The central layer may be substantially free of free cellulose fibers which are not integrated with the other fibers of the nonwoven. The amount of such free cellulose fibers in the absorbent core may be less than 10% by weight of the total absorbent core, or less than 5% by weight of the total absorbent core, or less than 1% by weight of the total absorbent core, or completely free of such free cellulose fibers. The high loft material may comprise at least 10%, 30% 50%, 70%, 90% and up to 100% by weight of the high loft layer, of synthetic fibers.

The fibers forming the central layer may be made partially or entirely of a relatively resilient synthetic fibers, in particular polypropylene (PP), polyamide (PA, such as nylons) or polyethylene terephthalate (PET) fibers. The diameter of the fibers may for example range from 0.01 mm to 0.50 mm. The thickness, basis weight and density of the central layer are typically homogenous in both transversal direction (x) and longitudinal direction (y). The orientation of fibers in the central layer may be in-homogenous such as predominant orientation of fibers into one direction x or y such as in carded nonwovens. Furthermore, the fiber orientation in the central layer in thickness direction z may be different versus the predominant orientation in one or both directions x and/or y.

The high loft central layer may in particular have a thickness of at least 0.30 mm, in particular ranging from 0.30 mm to 2.00 mm, or from 0.50 mm to 1.5 mm, as measured at a pressure of 4.14 kPa (0.6 psi) (according to the test method described further below).

The high loft layer may in particular have a thickness ranging from 0.30 mm to 2.50 mm or from 0.5 to 2.0 mm or from 0.7 to 1.3 mm, as measured at a pressure of 0.83 kPa (0.12 psi) (according to the test method described further below).

The basis weight of the high loft central layer may for example range from 15 gsm to 500 gsm, in particular from 20 gsm to 200 gsm, more particularly of from 30 gsm to 100 gsm.

The values indicated herein for the central layer are considered for the high loft material taken in isolation, that is before the SAP particles have been deposited between the fibers or an adhesive applied to it, unless indicated otherwise. When the absorbent core comprises two or more high loft central layers, these may be the same or different.

While the invention is not limited to a specific type of nonwoven or fibers, a particular example of suitable nonwoven layer are bonded carded webs ("BCW"). "Bonded carded web" refers to nonwovens that are made from staple fibers that are sent through a combing or carding unit, which separates and generally aligns the staple fibers in the machine direction to form a generally machine direction-oriented fibrous nonwoven web. This web can then be drawn through a heated drum, creating bonds throughout the fabric without applying specific pressure (through air bonding process). Such trough air bonded carded web (TABCW) material provides a low density, lofty through-air bonded carded web. Examples of suitable TABCW are for example disclosed in WO2000/71067 (KIM DOO-HONG et al.). The carded webs may also be bonded by other methods, such as mechanical entanglement of the fibers (needle punching for example).

In a carded nonwoven, the fibers in the web are aligned predominantly in the machine direction and have a more uniform fiber alignment than other nonwovens, which results in greater stability and internal bond strength especially in machine direction. The bonding technique chosen influences the integrity of the fabric. Through-air bonded carded web have excellent softness, bulk and compressibility, and rapid strike through and good rewet. Synthetic, natural and recycled fibers in a wide range of deniers can be used. Soft PE/PP bicomponent staple fibers may in particular be used. The carded nonwoven material can for example comprise about 3 to about 10 denier staple fibers. Carded nonwovens are also available directly from all usual suppliers of nonwoven webs for use in absorbent articles, for example Fitesa Ltd or Fiberweb Technical Nonwovens.

The high loft layer may also be a spunmelt nonwoven. Spunmelt is a generic term describing the manufacturing of nonwoven webs directly from thermoplastic polymers. It encompasses two processes and the combination of both: spunlaid (also known as spunbond) nonwoven and meltblown nonwoven. In a spunlaid process, polymer granules are melted and molten polymer is extruded through spinnerets. The continuous filaments are cooled and deposited onto a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web.

The periphery of the central layer 43 typically defines the front edge 280, a back edge 282 and two longitudinally-extending side edges 284, 286 of the absorbent core 28. The front and back edges are typically shorter than the side edges. The front edge of the central layer corresponds to the edge intended to be placed towards the front edge of the absorbent article in which the core is or will be integrated.

Figure 6:
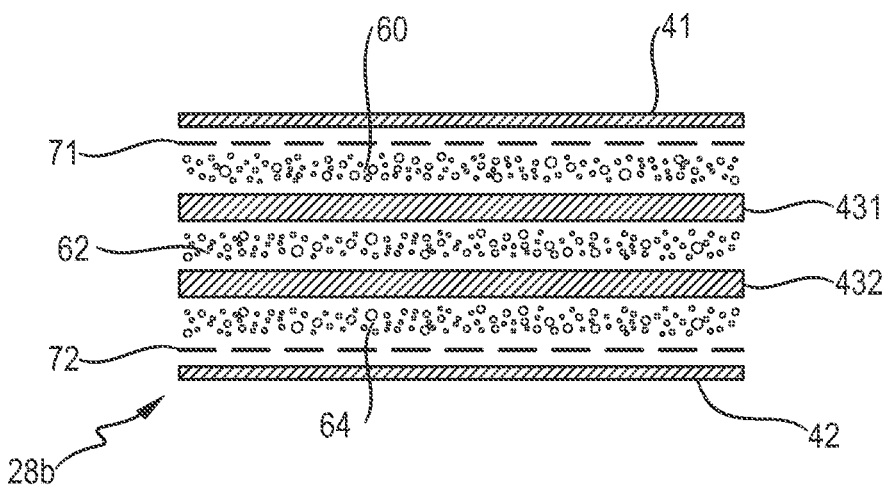
FIG. 6 shows a schematic cross-sectional of an alternative absorbent core comprising two central high loft layers.

The superabsorbent material may be distributed homogeneously at the surface of the core. Alternatively it can be profiled, with higher amount of SAP towards the front half of the core relative to the back half of the core. This is because there is typically more fluid discharged towards the front of the article in which a core will be incorporated. In addition to the profiled SAP distribution in the longitudinal direction (y), the SAP may be also be profiled in the transversal direction (x). Typically, the SAP is however homogenously distributed in the transversal (x) and the longitudinal direction (y), which simplifies production: in that case any of the two shorter sides may be considered as the front edge and the opposite side will be the back edge. The absorbent cores may comprise one, two, or more of high loft central layer. An absorbent core comprising two high loft central layers is discussed further below with reference to FIG. 6.

The central layer (or layers) serves as substrate for the SAP particles 60, 62 which are at least partially distributed within its pores. The SAP particles may be substantially uniformly blended across the thickness of the high loft layer. However, the SAP particles may be distributed heterogeneously in the vertical direction. The SAP particles are typically deposited on one side of the nonwoven and drawn into the high loft nonwoven for example by gravity or a negative pressure on the opposite side of the nonwoven. In this way, some particles remain close to the surface of the high loft central layer and other, typically smaller, particles may penetrate deeper within the pores of the high loft nonwoven. The SAP particles which are not trapped within the pores of the high loft layer but remain at the surface may be further immobilized by a layer of adhesive 71 or 72. The adhesive may be applied on the top and bottom cover layers first before being combined while still tacky with the high loft central layer. Typically the SAP particles are applied sequentially on the high loft layer from each side of the high loft layer as a first layer 60 of SAP and a second layer 62 of SAP, as further illustrated in FIG. 8. This process for SAP particles deposition may result in a SAP z-distribution pattern inside the central layer comprising two or more peaks of density separated by at least one buffer zone, when seen in the z direction.

Top Cover Layer 41 and Bottom Cover Layer 42

The high loft central layer 43 is sandwiched between a top cover layer 41 and a bottom cover layer 42. The top cover layer 41 is on the side of the core intended to be placed closest to the wearer-facing side of the absorbent article. The top cover layer is thus liquid-permeable, so that a fluid can easily reach the central layer through the top cover layer during use. The bottom cover layer is positioned on the other side of the central layer. It may be liquid-permeable or liquid impermeable. The top cover layer and the bottom cover layer provide a cover on both sides of the central layer for preventing the SAP particles from falling out of the high loft during the core and article making process and/or during use of the absorbent article.

The top and bottom cover layers may be made of a relatively thin and cheap material, as are commonly used for the production of conventional cores. The top and bottom cover layers may be for example a tissue paper (airfelt or wetlaid) having a basis weight ranging for example from 5 to 50 gsm, in particular 10 to 30 gsm. The top and bottom cover layers may also be formed from a low basis weight nonwoven web having a basis weight of between 5 gsm and 30 gsm, such as a carded nonwoven, spunbond nonwoven ("S") or meltblown nonwoven ("M"), and laminates of any of these. For example, spunmelt polypropylene nonwovens are suitable, in particular those having a laminate web SMS, or SMMS, or SSMMS, structure, and having a basis weight range of about 5 gsm to 20 gsm. Such materials are for example disclosed in U.S. Pat. No. 7,744,576, US2011/0,268,932A1, US2011/0319848A1 and US2011/0,250,413A1. Nonwovens materials are typically inherently hydrophobic, and the top cover layer may thus be treated to render it hydrophilic, for example by treating it with a surfactant or other methods as is known in the art. The top cover layer and the bottom cover layer may be made of the same or different material, optionally with the top cover layer or bottom cover layer treated differently to render to the top cover layer more hydrophilic than the bottom cover layer.

Figure 3:
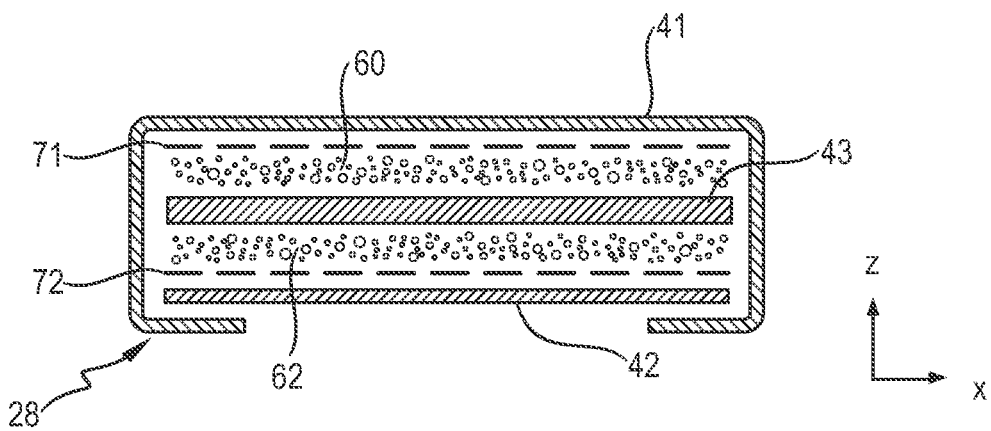
FIG. 3 shows a schematic exploded cross-sectional view of an alternative absorbent core.
Figure 4:
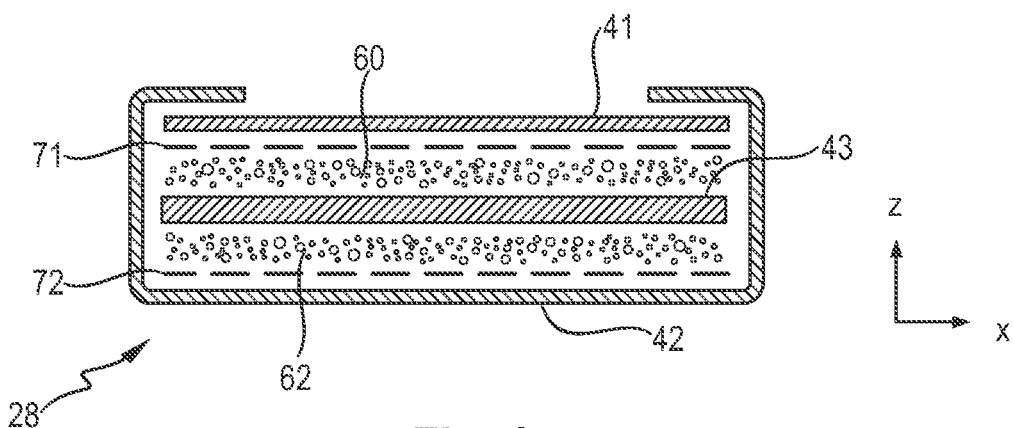
FIG. 4 shows a schematic cross-sectional view of an alternative absorbent core.

The top cover layer 41 can be wider than the bottom cover layer 42 so that this excess material can be folded around the longitudinal side edges 284, 286 of the core to form a C-wrap seal over the bottom cover layer 42, as illustrated in FIG. 3. Alternatively the bottom cover layer 42 can be wider than the top cover layer 41 so that this excess material can be folded around the longitudinal side edges 284, 286 of the core to form a C-wrap seal over the top cover layer 41, as illustrated in FIG. 4.

Figure 5:
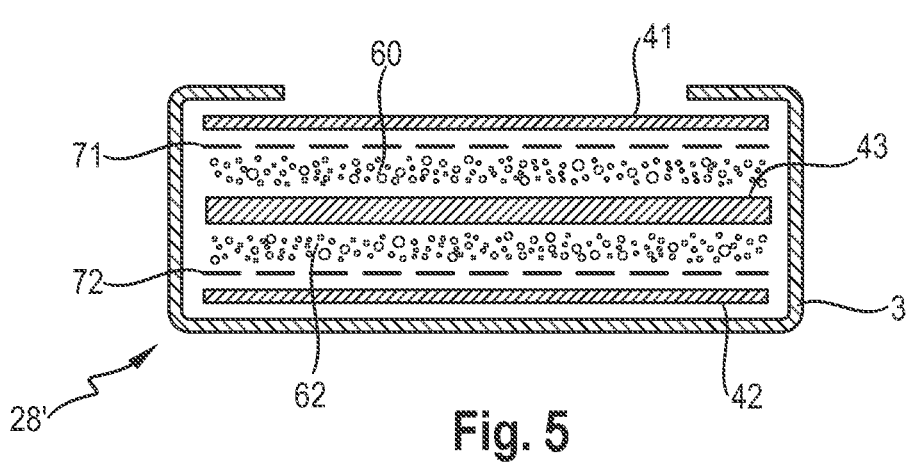
FIG. 5 shows a schematic cross-sectional view of an absorbent core as in FIG. 2 with a core wrapping layer.

In addition to the top cover layer and the bottom cover layer, the absorbent core can further comprise a wrapping layer 3 that encompasses the high loft central layer and the two cover layers, such by forming a C-wrap around the longitudinally extending side edges 284, 286 of the core, as shown in FIG. 5. By "C-wrap", it is meant that the layer covers at least the top side or bottom side of the core, extends along its side edges to form flaps that are then folded and attached, typically by gluing, over the opposite side of the core. The wrapping layer 3 may thus have a cross-section similar to the letter C (when rotated 90°). A C-wrap construction may further help containing the SAP particles during the making or wearing of the absorbent article. The wrapping layer may for example be made of a low basis weight nonwoven layer, for example having a basis weight of from 5 to 40 gsm, in particular from 8 to 25 gsm, in particular a SMS nonwoven, but other materials are of course possible. The wrapping layer 3 has been represented in FIG. 5 as extending from the bottom side of the core and having flaps folded over the top side of the core. The inverted configuration is also possible, with the C-wrapped layer 3 extending from the top side and with the flaps folded over the bottom side. The folded flaps may end and be attached in the vicinity of the longitudinally extending side edges of the core or may be longer than represented to that they overlap and attached to another. It is also considered that a C-wrap construction may be formed by one of the top cover layer or bottom cover layer extending transversally along the longitudinally extending side edges of the core and forming flaps as described for the wrapping layer 3. The presence of a wrapping layer is optional but is preferred especially if the top cover layer and the bottom cover layer are not sealed along their longitudinal sides.

The top cover layer 41 and/or the bottom cover layer 42 are preferably attached to the central layer 43. A layer of glue 71 may be for example applied between the top cover layer and the central layer 43. Any type of conventional glue and glue application method may be used. Typically, a hot melt glue may be sprayed on substantially the whole of the surface of the layers before putting the two layers in close contact so that they become attached. The glue may also be applied by a contact method to one of the layers, in this case in particular the top or bottom cover layer, typically by slot-coating a series of parallel thin lines of glue in the machine direction (y direction). A layer of glue 72 may also be similarly applied between the bottom cover layer 42 and the central layer 43. These layers of glue also have the advantages that they can immobilize the SAP particles in the dry state that have not penetrated within the central layer during the making of the core.

Superabsorbent Polymer Particles 60, 62, 64

SAP are water-insoluble but water-swellable cross-linked polymers capable of absorbing large quantities of fluids. SAP are in particulate form so as to be flowable in the dry state. Typical particulate SAP are polyacrylate polymers, however it is not excluded that other polymer materials may also be used. For example, starch-based particulate absorbent polymer material may also be used, as well polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

SAP may be polyacrylates and polyacrylic acid polymers that are internally and/or surface cross-linked. The superabsorbent polymer of the invention may be selected from polyacrylates and polyacrylic acid polymers that are internally and surface cross-linked. The superabsorbent polymers can be internally cross-linked, i.e. the polymerization is carried out in the presence of compounds having two or more polymerizable groups which can be free-radically copolymerized into the polymer network. Exemplary superabsorbent polymer particles of the prior art are for example described in WO2006/083584, WO2007/047598, WO2007/046052, WO2009/155265, WO2009/155264. Preferably, the SAP particles comprise crosslinked polymers of polyacrylic acids or their salts or polyacrylates or derivatives thereof.

The absorbent core of the invention comprises at least two different types of SAP. The first SAP particles are referred herein as "SAP1" and the second SAP particles are referred herein as "SAP2", and both collectively as SAP. Both SAP1 and SAP2 are in the form of particles, and are deposited on the top surface and the bottom surface of the high loft central layer respectively. The SAP particles are typically deposited sequentially on each side of the high loft layer, with the high loft layer side being laminated and flipped in between the depositions. The SAP particles can at least partially penetrate within the pores of the high loft layers during the deposition step, so that they are at least partially distributed within the high loft central nonwoven. The particles are thus immobilized within the pores of the high loft layer on one hand, and by the tissue or nonwoven layer laminated on each of the top and bottom surface of the high loft central layer.

The term "superabsorbent polymer" (herein abbreviated as "SAP" in the singular and plural form) typically refers to absorbent materials that can absorb at least 10 times their weight of an aqueous 0.9% saline solution as measured using the Centrifuge Retention Capacity (CRC) test (EDANA method NWSP 241.0.R2 (19)), referred herein as capacity. The SAP used in the present invention are preferably highly absorbent, with SAP1 having a higher capacity than SAP2.

The capacity of SAP1 may be of at least 30 g/g, preferably in the range of from 32 g/g to 50 g/g, and the capacity of SAP2 may be of at least 20 g/g, preferably in the range of from 25 g/g to 45 g/g. The capacity of SAP1 may be at least 2 g/g, preferably at least 4 g/g, higher than the capacity of SAP2.

The UPM Test method typically measures the flow resistance of a preswollen layer of superabsorbent polymer particles, i.e. the flow resistance is measured at equilibrium. Therefore, such superabsorbent polymer particles having a high UPM value exhibit a high permeability when a significant volume of the absorbent article is already wetted by the liquid exudates. These embodiments exhibit good absorption properties not only at the first gush but also at the subsequent gushes.

The UPM permeability may be expressed in UPM value, where 1 UPM unit is $1 \times 10^{-7}$ (cm3·s)/g. According to the invention, the permeability of SAP2 is of more than 5 UPM units, and is furthermore preferably higher than the permeability of SAP1. The permeability at equilibrium is measured using the UPM method described further below. The UPM value is measured according to the UPM Test method described herein. This method is closely related to the SFC test method which has been used in some of the prior art.

The permeability of SAP2 is preferably more than $6 \times 10^{-7}$ cm3·s/g, or at least $7.5 \times 10^{-7}$ cm3·s/g, or at least $10 \times 10^{-7}$ cm3·s/g, or at least $15 \times 10^{-7}$ cm3·s/g, preferably in the range of from $30 \times 10^{-7}$ cm3·s/g to $70 \times 10^{-7}$ cm3·s/g. The permeability of SAP2 may be of at least $5 \times 10^{-7}$ cm3·s/g higher than the permeability of SAP1, preferably at least $10 \times 10^{-7}$ cm3·s/g higher the permeability of SAP1.

Superabsorbent material having the required properties may be sourced from commercial suppliers, which have a wide range of SAP property available. Typically capacity and permeability are in trade-off, as one SAP having high capacity may have relatively low permeability and vice-versa.

The SAP particles may be relatively small (under 1 mm in their longest dimension) in their dry state and may be roughly circular in shape, but granules, fibers, flakes, spheres, powders, platelets and other shapes and forms are also known to persons skilled in the art. Typically, the SAP may be in the form of spherical-like particles. The absorbent material may thus consist or consist essentially of the SAP distributed within the high loft nonwoven.

Some of SAP particles may be agglomerated, as e.g. taught in EP3,391,961A1 (Kamphus, P&G). The agglomerated superabsorbent polymer particles may be obtained by various methods. Agglomerated particles may be for example obtained by aggregating the precursor particles with an interparticle crosslinking agent reacted with the polymer material of the precursor particles to form crosslink bonds between the precursor particles have been for example disclosed in U.S. Pat. Nos. 5,300,565, 5,180,622, (both to Berg), U.S. Pat. Nos. 5,149,334, 5,102,597 (both to Roe), U.S. Pat. No. 5,492,962 (Lahrman) Other ways to obtain agglomerated SAP particles are for example described in EP3056521B1 (Kim et al.), EP1512712B1 (Koji et al.), U.S. Ser. No. 10/414,876B2 (Jang et al.), U.S. Pat. No. 7,429,009B2 (Nagasawa et al), EP220224911 (Higashimoto et al), EP2011803B1 (Handa et al).

Agglomerated superabsorbent polymer particles may also be obtained by a method comprising the steps of providing superabsorbent polymer particles and mixing the superabsorbent polymer particles with a solution comprising water and a multivalent salt having a valence of three or higher. This method is further disclosed EP2,944,376A1. The superabsorbent polymer particles of the core of the invention may in particular comprise at least 5%, or at least 10%, or at least 20%, or at least 30%, or at least 40%, or at least 50% by weight of the agglomerated superabsorbent polymer particles The surface of the SAP particles may be coated. The surface of the SAP may be surface crosslinked. The SAP particles may also comprise surface and/or edge modified clay platelets. Preferably, the clay platelets are montmorillonite, hectorite, laponite or mixtures thereof. Preferably, the clay platelets are laponite. The SAP may comprise from 0.1 to 5% by weight of clay platelets with modified surfaces and/or edges compared to the weight of the precursor superabsorbent polymer particles.

SAP can also be characterized by the time it takes them to reach an uptake of 20 g/g of less than 220 s, so-called T20, as measured by the SAP K(t) test method described below. Any of SAP1 and/or SAP2 may in particular have a T20 in the range of from 100 s to 220 s. The SAP1 or SAP2 or both SAP T20 values may be less than 200 s, or less than 180 s, or less than 160 s. The time T20 may also be of at least of 100 s, 104 s, 120 s or 140 s, and any combinations of these upper and lower values to form a range, e.g. of from 100 s to 200 s.

SAP having the required T20 can be synthesized using for example the teaching of WO2015/041,784A1 which discloses SAP having a T20 ranging of from 104 s to 211 s. The SAP having a desired T20 may also be acquired directly from conventional SAP suppliers. For example, the inventive example below uses a SAP bought via Amazon under product name SCHAUCH HYDE 235, "Der Alleskoenner", having a measured SAP T20 of 165 s.

Unless otherwise indicated, the values indicated herein to qualify the SAP (e.g. CRC capacity, UPM permeability, AAP, T20 . . . ) refer to the properties of the SAP considered as raw material as it supplied. These properties should be measured as much as possible before the absorbent core is manufactured as otherwise it may be difficult to separate the SAP from the finished absorbent core, as some of the larger particles may be partially glued to the top or bottom substrate layer, and the smaller particles may have moved further within the pores of the high loft layers.

The total amount of SAP present in the absorbent core may also vary according to expected user of the article. Diapers for newborns require less SAP than infant or adult incontinence diapers. The total amount of all SAP in the core may be for example comprised from about 2 g to 50 g, in particular from 5 g to 40 g, or for 10 g to 20 g for typical enfant diapers. The absorbent core may typically comprise from 3 g to 10 g of SAP1, and/or from 3 g to 10 g of SAP2. The basis weight for all SAP within the absorbent core may be for example of at least 50, 100, 200, 300, 400, 500 g/m2 or more, or from 200 to 400 g/m². The average basis weight of SAP1 may be of at least 50 g/m2, preferably from 100 g/m2 to 300 g/m2. The average basis weight of SAP2 may be of at least 50 g/m2, preferably from 100 g/m2 to 300 g/m2. The average basis weight is calculated by dividing the weight of the SAP considered by the surface of the high loft central layer.

The absorbent core may typically comprise at least 60% by weight of superabsorbent polymer particles (all SAP added), preferably at least 70%, by total weight of the core.

Process for Making

Figure 8:
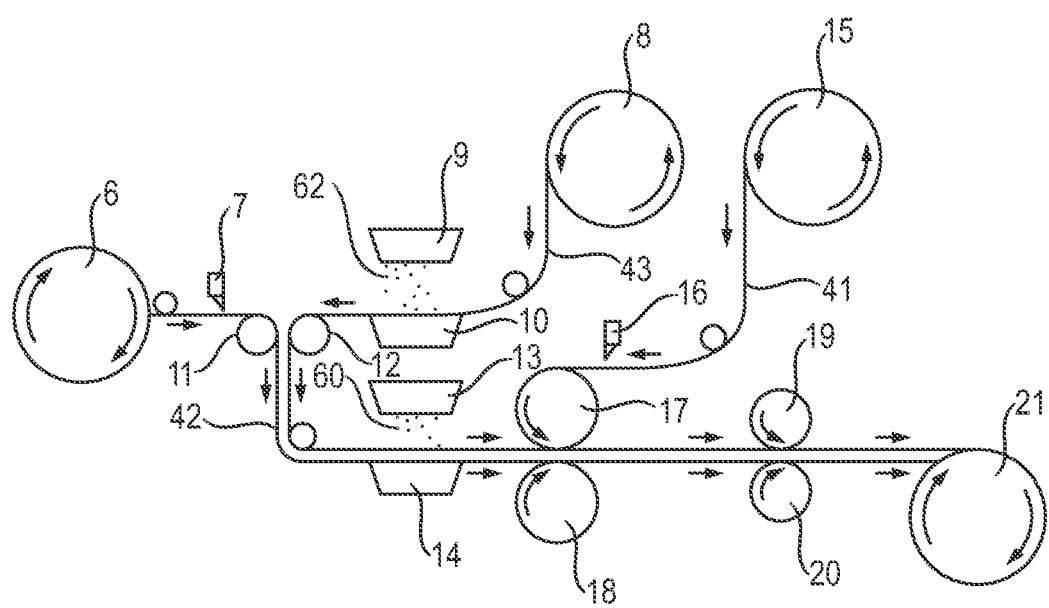
FIG. 8 is a schematic sketch of a process for making an absorbent core of the invention.

An exemplary continuous process for making the absorbent cores is illustrated in FIG. 8. The process and apparatus discussed above is generally similar to the one disclosed in CN101797201 or in FIG. 3 of WO2020/025401 (BASF, Ge et al.). The various arrows in this Figure represent the rotational directions of the various roll-releasing cylinders and roll-winding cylinders and the running directions of the manufacturing materials during the production flow process. Other processes and modifications are of course possible.

As illustrated in FIG. 8, the apparatus for making the absorbent cores may include a bottom cover layer web unwinder 6, a bottom cover layer glue spraying head 7, a high loft central layer web unwinder 8, a first SAP particles dispenser 9 and optional vacuum suction box 10, a first pair of rollers 11 and 12, a second SAP particles dispenser 13 and optional vacuum suction box 14, a top cover layer web unwinder 15, a top cover layer spraying head 16, second pair of rollers 17 and 18, trimming off knives 19, 20, and a product roll winding roller 21.

The first and second SAP particles dispenser 9, 13 may be both provided with a frequency changing and speed adjusting device (not drawn in FIG. 8), adjusted to maintain a vibration frequency that matches the product roll winding roller 21 linear velocity and to ascertain that the deposited SAP is mostly uniformly distributed on the high loft web 43.

During production, a roll of bottom cover layer material 42, for example a paper or nonwoven roll, is installed on the bottom cover layer web unwinder 6. A high loft nonwoven fabric roll 43 is installed on the central layer web unwinder 8. The initial density and thickness of the high loft central layer may be conveniently measured on the raw material Thickness and Density Measurement Method further described below.

The SAP particles are charged in the first and second SAP particles sieve plates 9 and 13. A roll of top cover layer material 41, which can be a paper or nonwoven roll, is installed on the top cover layer web unwinder 15. During the continuous process of making the absorbent cores, the bottom cover layer 42 passes through the spraying head 7 and is applied on one side with a glue 72, before being attached to the central layer 43 between the first press rollers 11 and 12. The high loft nonwoven central layer 43 passes through the first SAP dispenser 9 and vacuum suction box 10, wherein the SAP particles 62 are deposited into the central layer and at least partially distributed into the fibers the central layer from a first side.

After the bottom cover layer 42 and the central layer 43 have been pressed together between the rollers 11 and 12, these combined layers may optionally pass between a second SAP particles sieve plate 13 and vacuum suction box 14 that cooperate to deposit SAP particles 60 onto the second surface of the central layer and blend the SAP particles in the fibers of the central layer from this second surface. The top cover layer 41 which has been applied with an adhesive 72 by a glue spraying head 16 is then joined to the central layer to cover the second surface of the central layer between two press rollers 17 and 18. Of course in the preceding the top cover layer and bottom cover layer may be used interchangeably.

The press rollers 17 and 18 may have a substantially flat surface, or they may have elevated areas where extra pressure and heat should be applied onto the core. These elevated areas may coincide with the channel areas, and thus provide a mechanical bonding, ultrasonic bonding and/or heat bonding within the channel zones 26. The press rollers 11-12, 17-18 may be heated. It is also possible that the rollers have elevated areas along the longitudinal side edges and/or the back and front edges (360° perimeter) the core. A better bonding can be achieved in these zones when they are free of SAP as in the channel zones 26. Trimming knives 19 and 20 can be provided to trim the longitudinal side edges of the continuous band of absorbent core before the stream of the absorbent core material is finally rolled into a roll of absorbent core material by the product roll winding roller 21.

The roll of absorbent core material thus formed may be stored or transported to an article production site where it is further converted into an absorbent product. It is also possible that instead of forming a roll, the stream of absorbent core material may be directly fed into a converting line, in which case the absorbent cores will be individualized by cutting along their front and back edges.

A wrapping layer 3 (not represented in FIG. 8) may also be fed before the core material is rolled to wrap the top, central and bottom cover layer as shown discussed in relation to FIG. 5 to prevent losses of SAP though the side edges of the absorbent core. Alternative such wrapping layer may also be attached to the core when further converting the core material web.

Cores 28b with Dual High Loft Nonwoven Layers 431, 432

The absorbent cores 28 discussed previously comprise a single high loft nonwoven layer, however it is also possible that the absorbent cores comprise two (or more) high loft nonwoven layers between the top and bottom cover layers. This is illustrated for example in FIG. 6, wherein an absorbent core 28b comprising a first central layer 431 and the second central layer 432 are shown sandwiched between the top cover layer 41 and the bottom cover layer 42.

The absorbent core 28b thus may comprise a first central layer 431 and a second central layer 432, each of which being a high loft fibrous nonwoven layer comprising for example three or more superabsorbent polymer particle layers 60, 62, 64 at least partially distributed within the pores of the high loft central layers. The two (or more) high loft central layers may be comprised of the same material or different high loft nonwovens. For example, the permeability in the upper central layer may be enhanced by using a low basis weight high loft and softness may be enhanced in the bottom cover layer with a denser high loft material. Of course, other configurations are also possible. The two or more two central layers can be of equal dimensions in the x,y plane of the core, but they may also have different length and/or width. Two central layers of unequal length could be beneficial to provide different amount of SAP along the absorbent core, and made for example by adding a cut and slit unit on the second layer patch, and before combining it with the first layer.

At least one of the two high loft central layers comprise two different types of SAP as discussed above, the first SAP (SAP1) having a higher capacity than the second SAP, as measured by the CRC method, and the second SAP (SAP2) having a UPM value of more than 5 UPM units, as measured by the UPM method, and preferably having a higher UPM value than SAP1. For example with SAP1 may be placed the SAP layer closest towards the top cover layer of the absorbent core (60) and the SAP2 layer may be one of the underlying layer (e.g. SAP layer 62 or 64 in FIG. 6).

Absorbent cores comprising a dual high loft nonwoven layers may be made by a method adapted from one of the methods disclosed above, see for example WO2016/106021A1 where two separate high loft layer releasing cylinders are described to provide for the first and second high loft central layers 431, 432. As an alternative, a high loft web having a double width may be used: such a large width roll can be cut after release in machine direction in two halves providing for two streams of high loft nonwoven material that are then separately deposited with SAP particles. The two streams of high loft material 431, 432 may be then combined separately with the top cover layer and bottom cover layer respectively, each having then SAP particles 60 deposited onto them through a suitable SAP deposition device.

Absorbent Article 20

Figure 7:
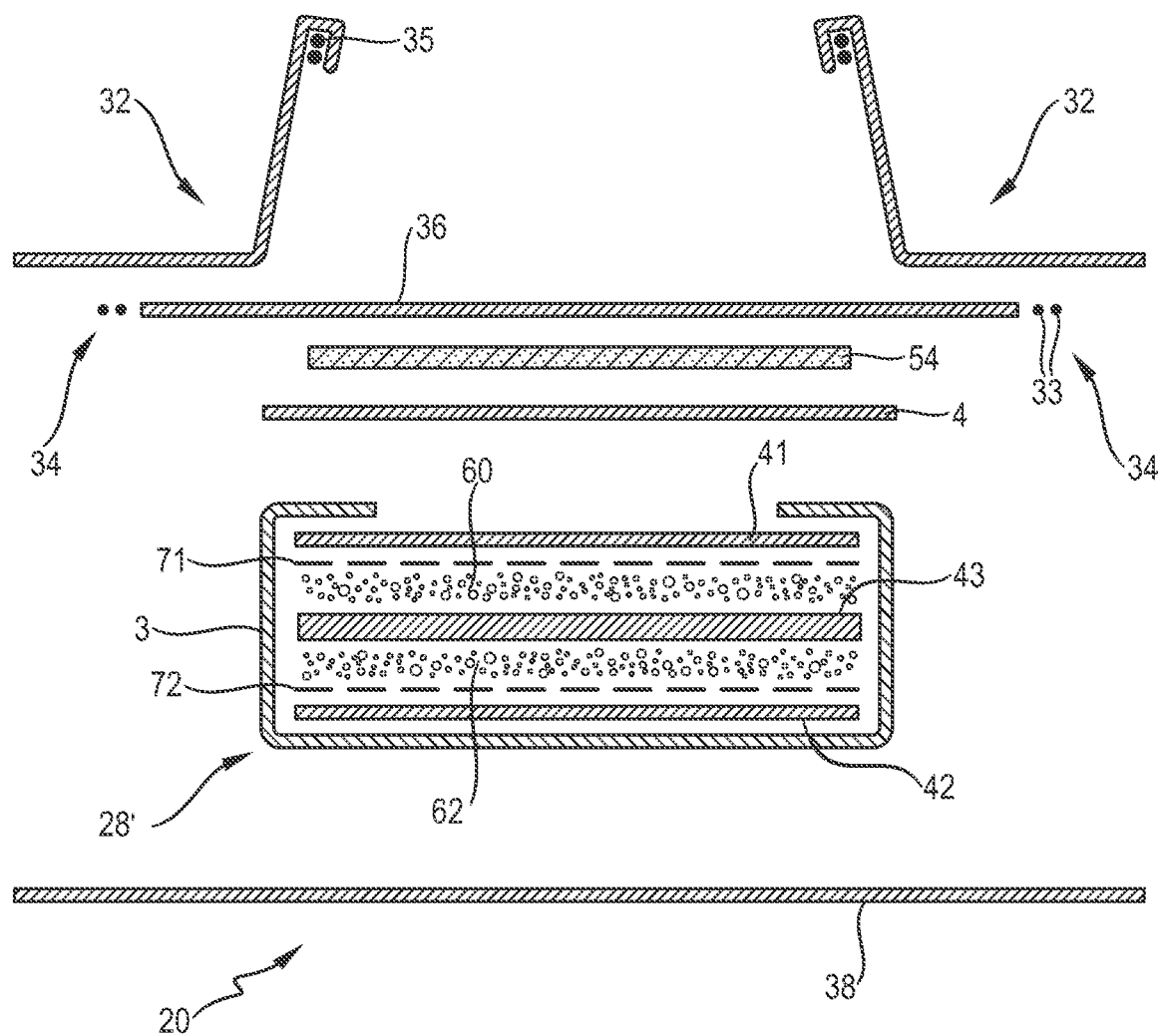
FIG. 7 shows a schematic cross-sectional of an absorbent article comprising the absorbent core of FIG. 5.

The absorbent cores may be incorporated into any kind of personal hygiene articles, in particular pant diapers and taped diapers, as well as inserts in hybrid systems comprising a washable outer cover and a disposable insert. A schematic cross-sectional view showing some of the main components of a diaper absorbent article 20 is illustrated in FIG. 7. In this Figure, the absorbent core of FIG. 5 (with a wrapping layer 3) is shown, but this is of course not limiting and for illustration only. Absorbent articles typically comprise a wearer-facing fluid permeable topsheet 36 and a garment-facing liquid impermeable backsheet 38 attached to each other along their perimeter. The absorbent core is placed between these layers and may be attached directly and indirectly to these layers, typically by gluing or heat/pressure bonding.

The topsheet 36 is preferably compliant, soft-feeling, and non-irritating to the wearer's skin. Further, at least a portion of the topsheet is liquid permeable, permitting liquids to readily penetrate through its thickness. A suitable topsheet may be manufactured from a wide range of materials, such as porous foams, reticulated foams, apertured plastic films, or woven or nonwoven materials of natural fibers (e.g., wood or cotton fibers or viscose), synthetic fibers or filaments (e.g., polyester or polypropylene or bicomponent PE/PP fibers or mixtures thereof), or a combination of natural and synthetic fibers. If the topsheet includes fibers, the fibers may be spunbond, carded, wet-laid, meltblown, hydroentangled, or otherwise processed as is known in the art, in particular spunbond PP nonwoven. Typical diaper topsheets have a basis weight of from about 10 gsm to about 28 gsm, in particular between from about 12 gsm to about 18 gsm but other basis weights are possible.

The backsheet 38 is typically impermeable to liquids (e.g. urine). The backsheet may for example be or comprise a thin plastic film such as a thermoplastic film having a thickness of less than about 0.10 mm Exemplary backsheet films include those manufactured by Tredegar Corporation, based in Richmond, VA, and sold under the trade name CPC2 film. Other suitable backsheet materials may include breathable materials which permit vapors to escape from the article while still preventing exudates from passing through the backsheet. A covering low basis weight nonwoven may be attached to the external surface of the film to provide for a softer touch.

The absorbent articles may also comprise a liquid management layer 54 (also called fluid acquisition or fluid distribution layer) directly under the topsheet 36. The function of such a layer is to rapidly acquire the fluid from the topsheet away from the wearer-facing side and/or to distribute over a larger area so it is more efficiently absorbed by the absorbent core. It is also possible that such a liquid management layer may be placed between the backsheet and the absorbent core. A further layer 4 may be present between the liquid management 54 and the absorbent core 28. The further layer 4 may be another such acquisition or distribution layer, or may be a tissue paper or low basis weight NW layer that provides an additional wrapping of the absorbent core 28' to avoid SAP particles from escaping outside the core.

Absorbent articles such as diapers or training pants may typically further comprise components that improve the fit of the article around the legs of the wearer, in particular barrier leg cuffs 32 and gasketing cuffs 34. The barrier leg cuffs may be formed by a piece of material, typically a nonwoven, which is partially bonded to the rest of the article and can be partially raised away and thus stand up from the plane defined by the topsheet. The barrier leg cuffs are typically delimited by a proximal edge joined to the rest of the article, typically the topsheet and/or the backsheet, and a free terminal edge intended to contact and form a seal with the wearer's skin. The standing up portion of the cuffs typically comprise an elastic element, for example one or a plurality of elastic strands 35. The barrier leg cuffs provide improved containment of liquids and other body exudates approximately at the junction of the torso and legs of the wearer.

In addition to the barrier leg cuffs, the article may comprise gasketing cuffs 34, which are formed in the same plane as the chassis of the absorbent article, in particular which may be at least partially enclosed between the topsheet or the barrier leg cuffs and the backsheet, and may be placed laterally outwardly relative to the upstanding barrier leg cuffs. The gasketing cuffs can provide a better seal around the thighs of the wearer. Usually each gasketing leg cuff will comprise one or more elastic string or elastic element 33 comprised in the chassis of the diaper for example between the topsheet and backsheet in the area of the leg openings.

The absorbent articles may also include other typical components found in diapers, training pants, replaceable inserts or adult incontinence products (and not further represented). A releasable fastening system for taped diapers may be provided to provide lateral tensions about the circumference of the absorbent article to hold the absorbent article on the wearer. This fastening system is not necessary for training pants since the waist region of these articles is already bonded. The fastening system usually comprises a fastener such as tape tabs, hook and loop fastening components, interlocking fasteners such as tabs & slots, buckles, buttons, snaps, and/or hermaphroditic fastening components, although any other known fastening means are generally acceptable. A landing zone is normally provided on the front waist region of the article for the fastener to be releasably attached.

The absorbent article may comprise front ears and back ears as is known in the art. The ears can be integral part of the chassis, for example formed from the topsheet and/or backsheet as side panel. Alternatively, they may be separate elements attached by gluing and/or heat embossing. The back ears are advantageously stretchable to facilitate the attachment of the tabs on the landing zone and maintain the taped diapers in place around the wearer's waist. The front ears may also be elastic or extensible to provide a more comfortable and contouring fit by initially conformably fitting the absorbent article to the wearer and sustaining this fit throughout the time of wear well past when absorbent article has been loaded with exudates since the elasticized ears allow the sides of the absorbent article to expand and contract.

Typically, adjacent layers will be joined together using conventional bonding method such as adhesive coating via slot coating or spraying on the whole or part of the surface of the layer, or thermo-bonding, or pressure bonding or combinations thereof. The bonding between components is for clarity and readability not represented in the majority of Figures, in particular FIG. 7, except for adhesive layers 71, 72. Adjacent layers of the article should be considered to be attached to another unless specifically mentioned otherwise. For example the backsheet and the bottom cover layer of the absorbent core may be typically glued together. The adhesives used may be any standard hotmelt glue as known in the art.

Packaging

The absorbent articles may be packaged in any type of conventional packaging. The absorbent articles may be in particular compressed when packaged to save space. In particular the package may comprise a plurality of the absorbent articles, wherein the package has an in-bag stack height of less than about 80 mm, according to the In-Bag Stack Height Test as described in U.S. Pat. No. 8,585,666 B2 (Weisman), incorporated herein by reference. Alternatively, packages of the absorbent articles of the present disclosure may have an in-bag stack height of from about 72 mm to about 80 mm or from about 74 mm to about 78 mm, specifically reciting all 0.5 mm increments within the specified ranges and all ranges formed therein or thereby, according to the In-Back Stack Height Test as described in U.S. Pat. No. 8,585,666B2 (Weisman)

EXAMPLES AND EXPERIMENTAL RESULTS a) SAP

The properties of different commercially sourced SAP were measured and are reported in Table 1 below. Values indicated in the tables with "n.a." were not measured. These SAP were used to make absorbent cores as indicated in Table 2.

TABLE 1

|  | SAP A | SAP B | SAP C | SAP D | SAP E | SAP F |
|---|---|---|---|---|---|---|
| CDC (g/g) | 27.75 | 36.6 | 33.1 | 30.1 | 30 | 29 |
| UPM ($10^{-7}$ cm3·s/g) | 5 | 1 | 7.5 | 45 | 45 | 31 |
| T20 (s) | 287 | n.a. | 260 | 250 | 250 | 112 |
| AAP at 0.7 psi (g/g) | 17.1 | 17.6 | 24.1 | 24.8 | 25 | 25.8 |

SAP B and SAP C are superabsorbent particles with a relatively high CRC, while SAP D, E and F have a relatively high permeability. SAP A had the lowest capacity and an intermediate permeability at 5 units.

b) Core Construction

Absorbent cores using different SAP combination were industrially produced on a core making line in a similar manner. In all cases, the central high loft layer was a 45 gsm air through bonded carded nonwoven (Haoyue) having a density of 0.021 g/cm3 and a caliper of 2.1 mm measured at 1.2 kPa. The top cover layer was a 23 gsm PP spunbond nonwoven, and the bottom cover layer a 32 gsm PET spunlace nonwoven.

Each individualized core comprised 6.375 g of the respective SAP1 deposited on the top side of the high loft layer (basis weight 170 gsm), and 5.775 g of the respective SAP2 on the bottom side of the high loft (basis weight 154 gsm). SAP1 and SAP2 were homogenously deposited on the respective side of the high loft central layer NW, a glue (Bostik) immediately sprayed and the respective cover layer laminated on each side. The amount and nature of the SAP used on each side of the core are indicated in the table 2 below.

TABLE 2

|  | Ex. 1 | Ex. 2 | Ex. 3 | Ex. 4 | C. Ex. 1 | C. Ex. 2 |
|---|---|---|---|---|---|---|
| SAP1 (top layer) | SAP B | SAP B | SAP B | SAP B | SAP B | SAP D |
| CRC (g/g) | 36.6 | 36.6 | 36.6 | 36.6 | 36.6 | 30.1 |
| UPM ($10^{-7}$ cm3·s/g) | 1 | 1 | 1 | 1 | 1 | 45 |
| SAP2 (bottom layer) | SAP C | SAP D | SAP E | SAP F | SAP A | SAP B |
| CRC (g/g) | 33.1 | 30.1 | 30 | 29 | 27.8 | 36.6 |
| UPM ($10^{-7}$ cm3·s/g) | 7.5 | 45 | 50 | 31 | 5 | 1 |

As can be seen, examples 1–4 are characterized by a SAP1 having higher capacity value than SAP2, and SAP2 having a UPM value of more than 5 UPM units. Comparative example 1 (C.Ex.1) has a SAP2 with a permeability value of 5 UPM units, and comparative example 2 (C.Ex.2) has a SAP1 with relatively low capacity and a SAP2 with a relatively high capacity in the bottom layer.

The different cores were incorporated in a commercial diaper chassis in a similar manner, and the diapers thus obtained were tested using the Curved Global Acquisition Method and Light Touch Dryness (cGAM-LTD) test, an internal method used to measure the time required to acquire three consecutive 75 ml saline gushes, and the rewet amount of diapers after each gush under low rewet pressure (at 0.03 psi) using an absorbent paper. Lower times cGAM for the different gushes and lower weight for the LTD values are advantageous. The results of the test are summarized in Table 3.

TABLE 3

|  | Ex. 1 | Ex. 2 | Ex. 3 | Ex. 4 | C. Ex1 | C. Ex. 2 |
|---|---|---|---|---|---|---|
| cGAM gush1 (s) | 103.2 | 111.6 | 97.1 | 76.2 | 109.0 | 90.5 |
| cGAM gush2 (s) | 352.5 | 342.6 | 331 | 324 | 501.6 | 294.0 |
| cGAM gush3 (s) | 781.3 | 760.1 | n.a. | n.a. | 1058.1 | 671.3 |

TABLE 3-continued

|  | Ex. 1 | Ex. 2 | Ex. 3 | Ex. 4 | C. Ex1 | C. Ex. 2 |
|---|---|---|---|---|---|---|
| 2nd LTD rewet/g | n.a. | n.a. | 0.038 | 0.048 | 0.294 | n.a. |
| 3rd LTD rewet/g | 0.358 | 0.201 | n.a. | n.a. | 0.816 | 0.447 |

Overall, Examples 2 and 3 have the best design with fast acquisition speed and the best rewet performance at second and third gushes. Examples 2-3 used a SAP with high CRC (36.6 g/g) as SAP1, and SAP2 with high UPM (45/50 units). Examples 1 and 4 have acceptable performance. Example 1 has similar design structure as Example 2, but with a SAP2 having a lower UPM (7.5 units), resulting in relatively slower acquisition speed and higher rewet.

Comparative Example 1 had the worst performance among the cores tested, using a SAP2 had both relatively low CRC and UPM in this example.

Comparative Example 2 has the fastest acquisition speed, possibly due to the high UPM permeability value of SAP1 across the three gushes. However, the rewet measured at 3rd LTD was high and overall this core design is thus deemed inferior to the examples 1-4, and in particular examples 2-3, as a good balance between speed of acquisition and rewet is desired.

Test Procedures
Centrifuge Retention Capacity (CRC)

The CRC measures the capacity of the superabsorbent polymer particles to absorb for free swelling in excess liquid. The CRC is measured according to EDANA method NWSP 241.0.R2 (19).

Absorption Against Pressure

The AAP is measured according to EDANA standard test NWSP 242.0 R2 (19), with the pressure used being 0.7 psi and 0.3 psi, as indicated as AAP@0.7 psi and AAP@0.3 psi, respectively.

Thickness and Density Measurement Method

This method is used to measure the thickness (caliper) of the high loft central layer in a standardized manner. The density can then be calculated from the thickness and the basis weight of the layer. Unless otherwise mentioned, the thickness and density are indicated for the high loft material in the absence of SAP particles. The measurement should preferably be made on the high loft material before it was converted into an absorbent core and thus free of SAP. If the starting material is not available, the high loft central layer can be obtained by carefully extracting it from an absorbent core, and removing the majority of SAP particles for example by careful shaking or suction. A freeze spray may be used to separate the central layer from the other layers. The samples should be kept at least 24 hours at 21° C.±2° C. and 50%±10% RH to equilibrate, in particular if they have been previously compressed.

Equipment: Mitutoyo manual caliper gauge with a resolution of 0.01 mm, or equivalent instrument.

Contact Foot: Flat circular foot with a diameter of 16.0 mm (±0.2 mm). A circular weight may be applied to the foot (e.g., a weight with a slot to facilitate application around the instrument shaft) to achieve the target weight. The total weight of foot and added weight (including shaft) is selected to provide the desire pressure, for example 4.14 kPa of pressure (0.6 psi) to the sample. The thickness can be determined at different pressures, using accordingly different weights applied to the foot. The thickness and density measurements indicate the applied pressure, for example measured at 4.14 kPa (0.6 psi) or 1.2 kPa.

The caliper gauge is mounted with the lower surface of the contact foot in a horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm
Stopwatch: Accuracy 1 second.

Sample preparation: The central layer is conditioned at least 24 hours as indicated above.

Measurement procedure: The layer is laid flat with the bottom side, i.e. the side intended to be placed towards the backsheet in the finished article facing down. The point of measurement, i.e. the middle of the sample, is carefully drawn on the top side of the layer, taking care not to compress or deform the layer. In the unlikely case that the high loft nonwoven layer is not homogeneous in the transversal direction or longitudinal direction, the values are measured in the center of a sample corresponding to the center of an absorbent core that would be made from the sample.

The contact foot of the caliper gauge is raised and the central layer is placed flat on the base plate of the caliper gauge with the top side of the core up so that when lowered, the center of the foot is on the marked measuring point.

The foot is gently lowered onto the sample and released (ensure calibration to "0" prior to the start of the measurement). The caliper value is read to the nearest 0.01 mm, 10 seconds after the foot is released.

The procedure is repeated for each measuring point. Ten samples are measured in this manner for a given material and the average thickness is calculated and reported with an accuracy of one tenth mm. The basis weight of each sample is calculated by dividing the weight of each sample by their area.

The density, in $g/cm^3$, is calculated by dividing the basis weight (in g/cm2) of the material by the thickness (in cm).

Urine Permeability Measurement (UPM) Test Method
Lab Conditions:

This test has to be performed in a climate conditioned room at standard conditions of 23° C.±2° C. temperature and 45%±10% relative humidity.

Urine Permeability Measurement System

This method determined the permeability of a swollen hydrogel layer 1318. The equipment used for this method is described below.

Figure 9:
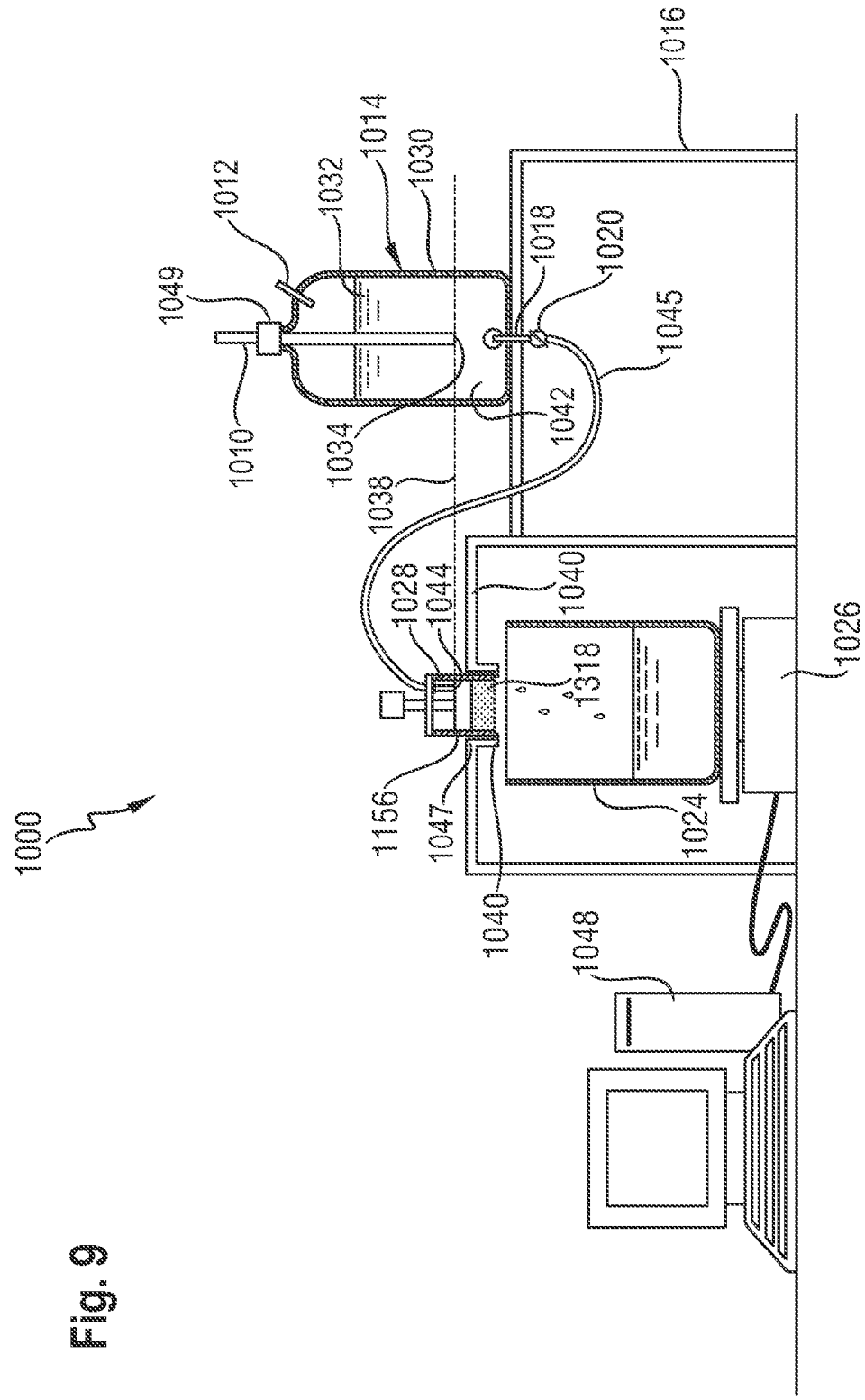
FIG. 9 is a partial cross-sectional side view of a suitable permeability measurement system for conducting the Urine Permeability Measurement Test.

FIG. 9 shows permeability measurement system 1000 set-up with the constant hydrostatic head reservoir 1014, open-ended tube for air admittance 1010, stoppered vent for refilling 1012, laboratory rack 1016, delivery tube 1018 with flexible tube 1045 with Tygon tube nozzle 1044, stopcock 1020, cover plate 1047 and supporting ring 1040, receiving vessel 1024, balance 1026 and piston/cylinder assembly 1028.

Figure 10:
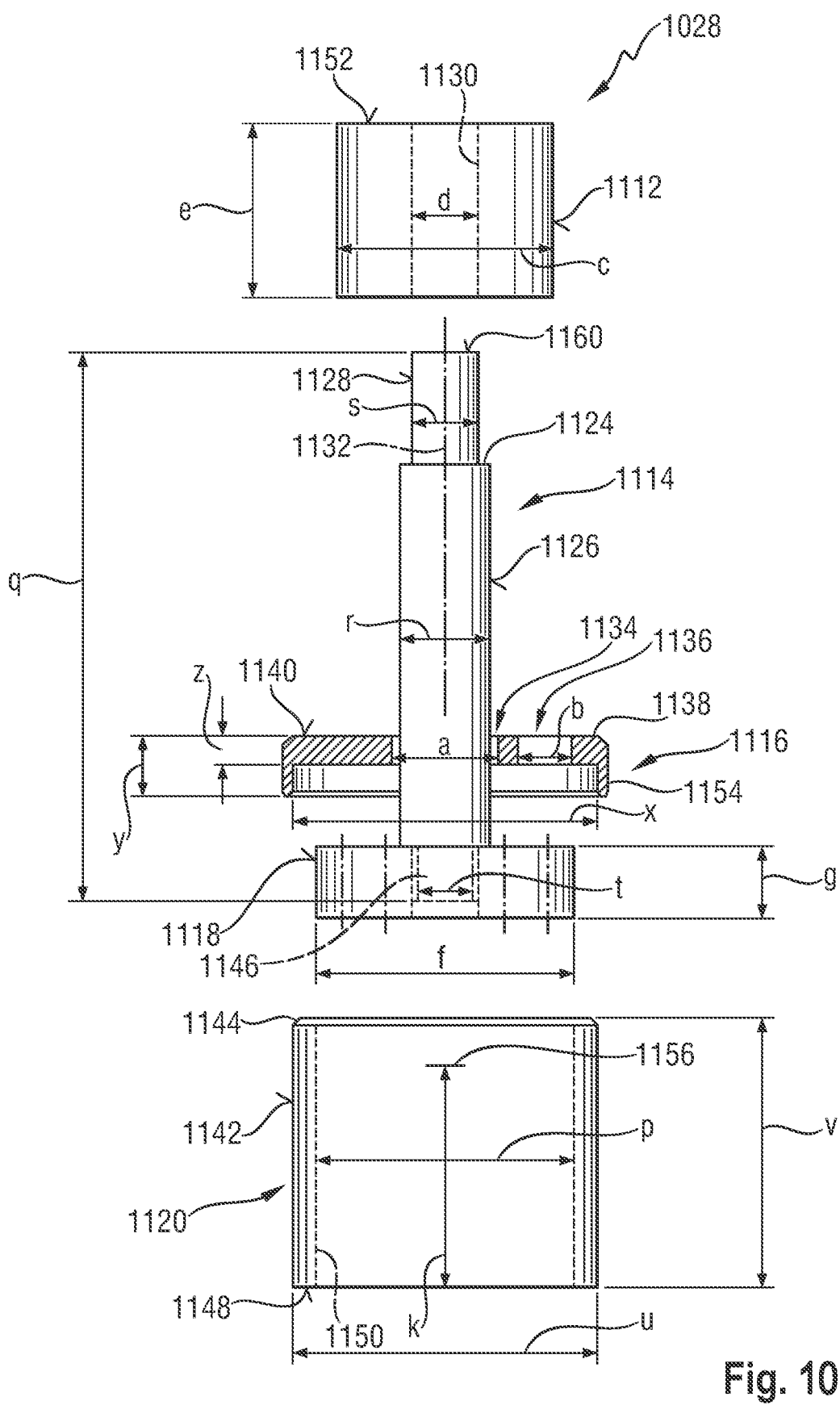
FIG. 10 is a cross-sectional side view of a piston/cylinder assembly for use in conducting the Urine Permeability Measurement Test.
Figure 11:
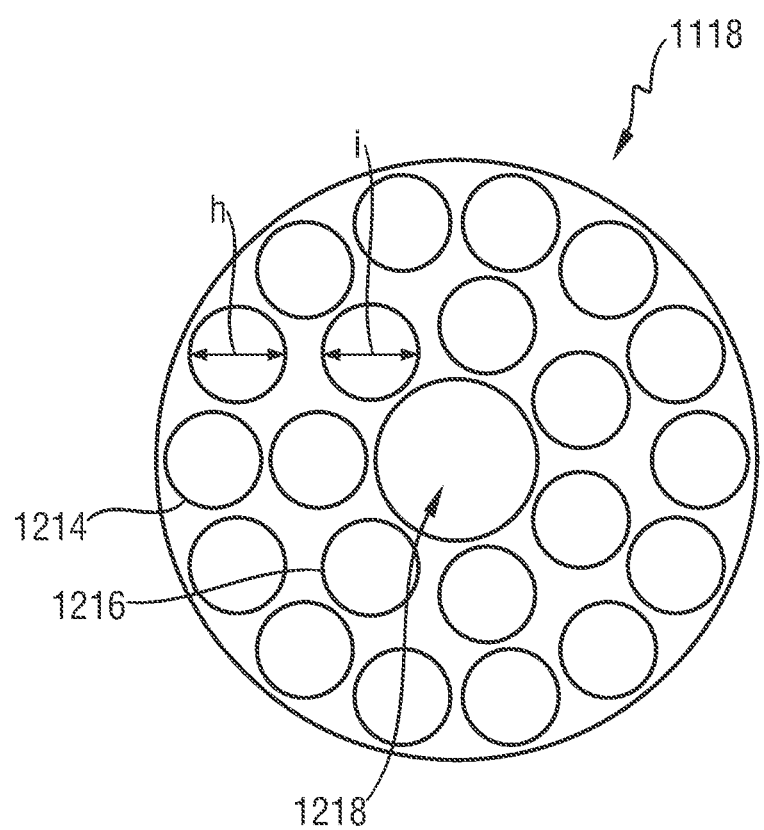
FIG. 11 is a top view of a piston head suitable for use in the piston/cylinder assembly shown in FIG. 10.

FIG. 10 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm2) with inner cylinder walls 1150 which are smooth. The bottom 1148 of the cylinder 1120 is faced with a stainless-steel screen cloth (ISO 9044 Material 1.4401, mesh size 0.038 mm, wire diameter 0.025 mm) (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 22.15 (±0.02) mm. An upper portion 1128 of the piston shaft 1114 has a diameter s of 15.8 mm, forming a shoulder 1124. A lower portion 1146 of the piston shaft 1114 has a diameter t of approximately ⅝ inch (15.9 mm) and is threaded to screw firmly into the center hole 1218 (see FIG. 10) of the piston head 1118. The piston head 1118 is perforated, made of transparent polycarbonate (e.g., Lexan®), and is also screened with a stretched stainless-steel screen cloth (ISO 9044 Material 1.4401, mesh size 0.038 mm, wire diameter 0.025 mm) (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the inner area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be repositioned with the same orientation relative to one another for each measurement.

The cylinder 1120 specification details are:
  Outer diameter u of the Cylinder 1120: 70.35 mm (±0.05 mm)
  Inner diameter p of the Cylinder 1120: 60.0 mm (±0.05 mm)
  Height v of the Cylinder 1120: 60.5 mm Cylinder height must not be lower than 55.0 mm!
The cylinder lid 1116 specification details are:
  Outer diameter w of cylinder lid 1116: 76.05 mm (±0.05 mm)
  Inner diameter x of cylinder lid 1116: 70.5 mm (±0.05 mm)
  Thickness y of cylinder lid 1116 including lip 1154: 12.7 mm
  Thickness z of cylinder lid 1116 without lip 1154: 6.35 mm
  Diameter a of first lid opening 1134: 22.25 mm (±0.02 mm)
  Diameter b of second lid opening 1136: 12.7 mm (±0.1 mm)
  Distance between centers of first and second lid openings 1134 and 1136: 23.5 mm
The weight 1112 specification details are:
  Outer diameter c: 50.0 mm
  Diameter d of center bore 1130: 16.0 mm
  Height e: 39.0 mm
The piston head 1118 specification details are:
  Diameter f: 59.7 mm (±0.05 mm)
  Height g: 16.5 mm Piston head height must not be less than 15.0 mm
  Outer holes 1214 (14 total) with a 9.30 (±0.25) mm diameter h, outer holes 1214 equally spaced with centers being 23.9 mm from the center of center hole 1218.
  Inner holes 1216 (7 total) with a 9.30 (±0.25) mm diameter i, inner holes 1216 equally spaced with centers being 13.4 mm from the center of center hole 1218.
  Center hole 1218 has a diameter j of approximately ⅝ inches (15.9 mm) and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the cover plate 1047 and supporting ring 1040 (with circular inner opening of not less than 64 mm diameter) above the receiving vessel 1024.

The cover plate 1047 and supporting ring 1040 are parts as used in the equipment used for the method "K(t) Test Method (Dynamic Effective Permeability and Uptake Kinetics Measurement Test method)" as described herein and is called "Zeitabhängiger Durchlassigkeitsprüfstand" or "Time Dependent Permeability Tester", Equipment No. 03-080578 and is commercially available at BRAUN GmbH, Frankfurter Str. 145, 61476 Kronberg, Germany Upon request, detailed technical drawings are also available.

Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 connected to a flexible tube 1045 (e.g. Tygon tube, capable to connect nozzle and reservoir outlet) and to a Tygon tube nozzle 1044 (inner diameter at least 6.0 mm, length appr. 5.0 cm) for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of approximately 12 mm, but not less than 10.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery flexible tube 1045 is dimensioned (e.g. outer diameter 10 mm) to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar 1049. The constant hydrostatic head reservoir 1014 can be positioned on a laboratory reck 1016 at a suitable height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 2.6 g/sec for at least 10 minutes.

The piston/cylinder assembly 1028 is positioned on the supporting ring 1040 in the cover plate 1047 or suitable alternative rigid stand. The salt solution 1032 passing through the piston/cylinder assembly 1028 containing the swollen hydrogel layer 1318 is collected in a receiving vessel 1024, positioned below (but not in contact with) the piston/cylinder assembly 1028.

The receiving vessel 1024 is positioned on the balance 1026 which is accurate to at least 0.001 g. The digital output of the balance 1026 is connected to a computerized data acquisition system 1048.

Preparation of Reagents (not Illustrated)

Figure 12:
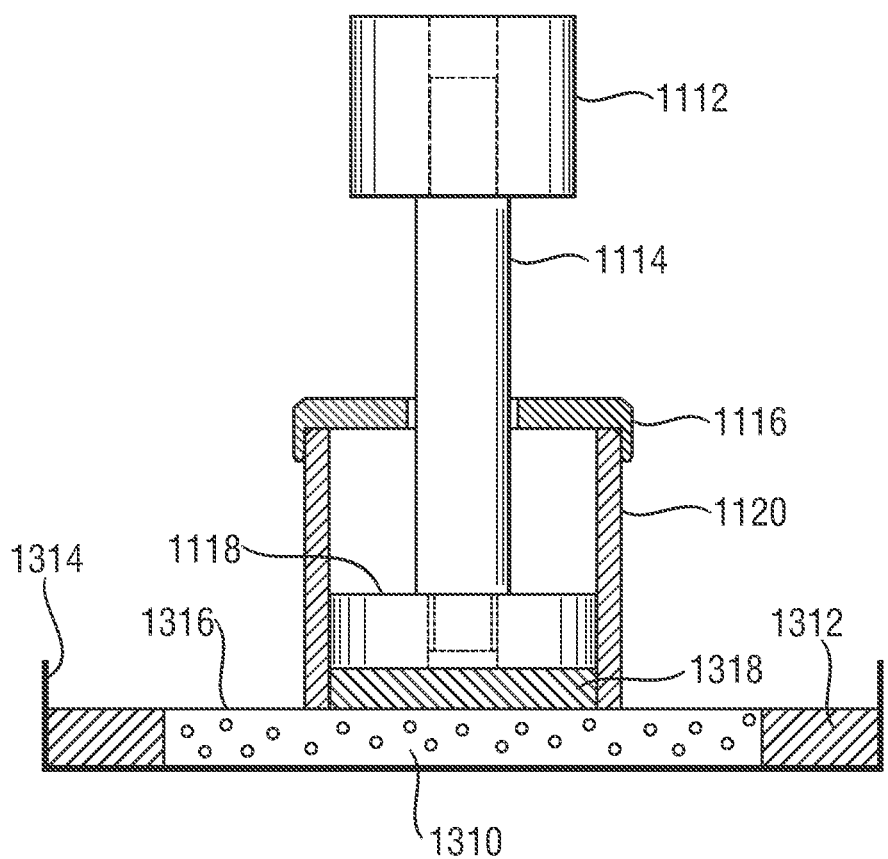
FIG. 12 is a cross-sectional side view of the piston/cylinder assembly of FIG. 10 placed on fritted disc for the swelling phase.

Jayco Synthetic Urine (JSU) 1312 (see FIG. 12) is used for a swelling phase (see UPM Procedure below) and 0.118 M Sodium Chloride (NaCl) Solution 1032 is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:

Potassium Chloride (KCl) 2.00 g
Sodium Sulfate (Na2SO4) 2.00 g
Ammonium dihydrogen phosphate (NH4H2PO4) 0.85 g
Ammonium phosphate, dibasic ((NH4)2HPO4) 0.15 g
Calcium chloride (CaCl2) 0.19 g—[or hydrated calcium chloride (CaCl2.2H2O) 0.25 g]
Magnesium chloride (MgCl2) 0.23 g—[or hydrated magnesium chloride (MgCl2.6H2O) 0.50 g]

To make the preparation faster, potassium chloride, sodium sulfate, ammonium dihydrogen phosphate, ammonium phosphate (dibasic) and magnesium chloride (or hydrated magnesium chloride) are combined and dissolved in the 80% of distilled water in the 1 L volumetric flask. Calcium chloride (or hydrated calcium chloride) is dissolved separately in approximately 50 ml distilled water (e.g. in a glass beaker) and the calcium chloride solution is transferred to the 1 L volumetric flask after the other salts are completely dissolved therein. Afterwards, distilled water is added to 1 L (1000 ml±0.4 ml) and the solution is stirred for a few minutes more. Jayco synthetic urine may be stored in a clean plastic container for 10 days. The solution should not be used if it becomes cloudy.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask (1000 ml±0.4 ml); and the flask is filled to volume with distilled water. A stir bar is added and the solution is mixed on a stirring plate until all the solids are dissolved.

The conductivity of the prepared Jayco solution must be in the range of appr. 7.48-7.72 mS/cm and of the prepared 0.118 M Sodium Chloride (NaCl) Solution in the range of appr. 12.34-12.66 mS/cm (e.g. measured via COND 70 INSTRUMENT without CELL, #50010522, equipped with Cell VPT51-01 C=0.1 from xs instruments or via LF 320/Set, #300243 equipped with TetraCon 325 from WTW or COND 330i, #02420059 equipped with TetraCon 325 from WTW). The surface tension of each of the solutions must be in the range of 71-75 mN/m (e.g. measured via tensiometer K100 from Kruess with Pt plate).

Test Preparation

Using a solid reference cylinder weight (not shown) (50 mm diameter; 128 mm height), a caliper gauge (not shown) (measurement range 25 mm, accurate to 0.01 mm, piston pressure max. 50 g; e.g. Mitutoyo Digimatic Height Gage) is set to read zero. This operation is conveniently performed on a smooth and level bench (not shown) of at least approximately 11.5 cm×15 cm. The piston/cylinder assembly 1028 without superabsorbent polymer particles is positioned under the caliper gauge (not shown) and a reading, L1, is recorded to the nearest 0.01 mm The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system 1048. The cover plate 1047 with the supporting ring 1040 is positioned above the receiving vessel 1024.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method NWSP 230.0.R2 (15) or via a Moisture Analyzer (HX204 from Mettler Toledo, drying temperature 130° C., starting superabsorber weight 3.0 g (±0.5 g), stop criterion 1 mg/140 s). If the moisture content of the superabsorbent polymer particles is greater than 3 wt %, then the superabsorbent polymer particles are dried to a moisture level of <3 wt %, e.g. in an oven at 105° C. for 3 h or e.g. at 120° C. for 2 h.

The empty cylinder 1120 is placed on a level benchtop 1046 (not shown) and the superabsorbent polymer particles are quantitatively transferred into the cylinder 1120. The superabsorbent polymer particles are evenly dispersed on the screen (not shown) attached to the bottom 1148 of the cylinder 1120 while rotating the cylinder 1120, e.g. aided by a (manual or electrical) turn table (e.g. petriturn-E or petriturn-M from Schuett). It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The weight 1112 is positioned on the upper portion 1128 of the piston shaft 1114 so that it rests on the shoulder 1124 such that the first and second linear index marks are aligned. The lid 1116 and piston shaft 1126 are then carefully rotated so as to align the third, fourth, fifth, and sixth linear index marks are then aligned with the first and the second linear index marks. The piston head 1118 (via the piston shaft 1114) is then gently lowered to rest on the dry superabsorbent polymer particles. Proper seating of the lid 1116 prevents binding and assures an even distribution of the weight on the hydrogel layer 1318.

Swelling Phase:

A fritted disc of at least 8 cm diameter (e.g. 8-9 cm diameter) and at least 5.0 mm thickness (e.g. 5-7 mm thickness) with porosity "coarse" or "extra coarse" (e.g. Chemglass Inc. # CG 201-51, coarse porosity; or e.g. Robu 1680 with porosity 0) 1310 is placed in a wide flat-bottomed Petri dish 1314 and JSU 1312 is added by pouring JSU 1312 onto the center of the fritted disc 1310 until JSU 1312 reaches the top surface 1316 of the fritted disc 1310. The JSU height must not exceed the height of the fritted disc 1310. It is important to avoid any air or gas bubbles entrapped in or underneath the fritted disc 1310.

The entire piston/cylinder assembly 1028 is lifted and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to ensure the hydrogel layer 1318 does not lose JSU 1312 or take in air during this procedure. The piston/cylinder assembly 1028 is placed under the caliper gauge (not shown) and a reading, L2, is recorded to the nearest 0.01 mm. If the reading changes with time, only the initial value is recorded. The thickness of the hydrogel layer 1318, L0 is determined from L2–L1 to the nearest 0.1 mm The piston/cylinder assembly 1028 is transferred to the supporting ring 1040 in the cover plate 1047. The constant hydrostatic head reservoir 1014 is positioned such that the delivery tube nozzle 1044 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer 1048 attached to the balance 1026, the quantity g (in g to accuracy of 0.001 g) of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation.

For each time period of 20 seconds (time $t(i-1)$ to $ti$) after the initial 60 seconds of the experiment, the respective flow rate $Fs(t)$ (in g/s) and the respective mid-point of the time $t(\frac{1}{2})t$ (in s) is calculated according to the following formulas:

$$Fs_{(t)} = \frac{(g_{(i-1)} - g_{(i)})}{(t_{(i-1)} - t_{(i)})} \text{ and } t_{(1/2)_t} = \frac{(t_{(i-1)} + t_{(i)})}{2} \quad (II)$$

The flow rate $Fs(t)$ of each time interval ($t(i-1)$ to $ti$) is plotted versus the mid-point of the time $t(\frac{1}{2})t$ of the time interval ($t(i-1)$ to $ti$). The intercept is calculated as $Fs(t=0)$.

Calculation of the Intercept:

The intercept is calculated via a best-fit regression line, e.g. as following: the equation for the intercept of the regression line, a, is:

$$a = y_{AVG} - b \cdot x_{AVG} \quad (III)$$

where the slope, b, is calculated as:

$$b = \frac{\sum (x - x_{AVG}) \cdot (y - y_{AVG})}{\sum (x - x_{AVG})^2} \quad (IV)$$

and where xAVG and yAVG are the sample means AVERAGE of the known_x's and AVERAGE of the known_y's, respectively.

Calculation of Urine Permeability Measurement Q:

The intercept $Fs(t=0)$ is used to calculate Q according to the following formula:

$$Q = \frac{F_s(t=0) \cdot L_0}{\rho \cdot A \cdot \Delta P} \quad (V)$$

where the flow rate $Fs(t=0)$ is given in g/s, L0 is the initial thickness of the hydrogel layer 1318 in cm, $\rho$ is the density of the salt solution 1032 in g/cm3 (e.g. 1.003 g/cm$^3$ at room temperature). A (from the equation above) is the area of the hydrogel layer 1318 in cm2 (e.g. 28.27 cm2), $\Delta P$ is the hydrostatic pressure in dyne/cm2 (e.g. 4920 dyne/cm$^2$), and the Urine Permeability Measurement, Q, is in units of cm3 sec/g. The average of three determinations should be reported.

| Variable | Description | Unit |
|---|---|---|
| gi | Mass of salt solution 1032 flown through the swollen gel layer (recorded by the balance) at the time ti (accuracy 0.001 g) | g |

| Variable | Description | Unit |
|---|---|---|
| ti | Time point (every 20 s) | s |
| t(½)t | Mid-point of time for the respective time interval ti − 1 to ti | s |
| Fst | Flow Rate at the time interval ti − 1 to ti | g/s |
| Fs (t = 0) | Intercept flow rate at t = 0 s from the plot of the flow rate Fs(t) vs. the mid-point of time t(½)t. | g/s |
| L0 | Thickness of the swollen gel layer (swollen with JSU 1312) before the salt solution 1032 flows through the gel layer. | Cm |
| ρ | Density of the salt solution 1032 (1.003 g/cm3) | g/cm3 |
| A | Area of the swollen gel layer (28.27 cm2) | cm2 |
| ΔP | Hydrostatic pressure across the gel layer (4920 dyne/cm2) | dyne/cm2 |
| Q | Urine Permeability Measurement | cm3 * sec/g |

SAP K(t) Test Method

This method determines the time dependent effective permeability SAP K(t) and the uptake kinetics of a gel layer formed from hydrogel-forming superabsorbent polymer particles or of an absorbent structure containing such particles under a confining pressure. The objective of this method is to assess the ability of the gel layer formed from hydrogel-forming superabsorbent polymer particles or the absorbent structure containing them to acquire and distribute body fluids when the polymer is present at high concentrations in an absorbent article and exposed to mechanical pressures as they typically occur during use of the absorbent article. Darcy's law and steady-state flow methods are used to calculate effective permeability (see below). (See also for example, "Absorbency," ed. By P. K. Chatterjee, Elsevier, 1982, Pages 42-43 and "Chemical Engineering Vol. II, Third Edition, J. M. Coulson and J. F. Richardson, Pergamon Press, 1978, Pages 122-127.)

In contrast to previously published methods, the sample is not preswollen therefore the hydrogel is not formed by preswelling hydrogel-forming superabsorbent polymer particles in synthetic urine, but the measurement is started with a dry structure. The equipment used for this method is called 'Zeitabhängiger Durchlassigkeitsprüfstand' or 'Time Dependent Permeability Tester', Equipment No. 03-080578 and is commercially available at BRAUN GmbH, Frankfurter Str. 145, 61476 Kronberg, Germany and is described below. Upon motivated request, operating instructions, wiring diagrams and detailed technical drawings are also available. A detailed description of the equipment and principle is further described in WO2015/041784 (P&G).

The SAP K(t) Test Method can be in particular used to measure the time required to reach an uptake of 20 g/g, starting at 0 s (t0) in s, the so-called T20. Using the test method, the time required to reach a certain uptake can be determined by linear interpolation. The time where the uptake of 20 g/g is first reached is called T20. The average values for T20 are reported from 3 replicates according to the accuracy required as known by the skilled man Misc.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core for use in an absorbent article, the absorbent core extending in a transversal direction and a longitudinal direction and having a thickness in a vertical direction perpendicular to the transversal direction and longitudinal direction, the absorbent core comprising:
    a liquid-permeable top cover layer;
    a bottom cover layer;
    a high loft central layer between the top cover layer and the bottom cover layer, the high loft central layer having a top surface oriented towards the top cover layer and a bottom surface oriented towards the bottom cover layer;
    a first superabsorbent polymer, SAP1, in the form of particles deposited on the top surface of the high loft central layer, wherein the SAP1 particles are substantially uniformly blended across a thickness of the high loft central layer, and the SAP1 particles are partially distributed in a z-distribution pattern comprising two or more peaks of density separated by at least one buffer zone, in the vertical direction within the high loft central nonwoven;
    a second superabsorbent polymer, SAP2, in the form of particles deposited on the bottom surface of the high loft central layer, wherein the SAP2 particles are substantially uniformly blended across the thickness of the high loft central layer, and the SAP2 particles are partially distributed in a z-distribution pattern comprising two or more peaks of density separated by at least one buffer zone, in the vertical direction within the high loft central layer;
    wherein each of SAP1 and SAP2 have a respective capacity as measured by the CRC method and a permeability as measured by the UPM test method, wherein SAP1 has a higher capacity than SAP2, and wherein the permeability of SAP2 is in the range of from $30 \times 10^{-7}$ cm3·s/g to $70 \times 10^{-7}$ cm3·s/g.

2. The absorbent core of claim 1, wherein SAP2 has a higher permeability than SAP1.

3. The absorbent core of claim 1, wherein the capacity of SAP1 is of at least 30 g/g.

4. The absorbent core of claim 1, wherein the capacity of the SAP1 is in the range of from about 32 g/g to about 50 g/g.

5. The absorbent core of claim 1, wherein the capacity of SAP1 is least 2 g/g higher than the capacity of SAP2.

6. The absorbent core of claim 5, wherein the capacity of SAP1 is least 4 g/g higher than the capacity of SAP2.

7. The absorbent core of claim 1, the permeability of SAP2 is higher than the permeability of SAP1 by at least $5 \times 10^{-7}$ cm3·s/g.

8. The absorbent core of claim 1, wherein the average basis weight of SAP1 is of at least 50 g/m$^2$ and the average basis weight of SAP2 is of at least 50 g/m$^2$.

9. The absorbent core of claim 8, wherein the average basis weight of SAP1 is of from about 100 g/m$^2$ to about 300 g/m$^2$ and the average basis weight of SAP2 is of from about 100 g/m$^2$ to about 300 g/m$^2$.

10. The absorbent core of claim 1, wherein the absorbent core comprises from about 3 g to about 10 g of SAP1, and from about 3 g to about 10 g of SAP2.

11. The absorbent core of claim 1, wherein the top cover layer and/or the bottom cover layer are each attached to the central high loft layer by a layer of glue, and wherein the layer of glue also immobilizes at least a portion of the SAP particles which are not distributed within the high loft central layer in the dry state.

12. The absorbent core of claim 1, further comprising a nonwoven wrapping layer at least partially wrapping the top cover layer, bottom cover layer and central layer.

13. The absorbent core of claim 1, wherein the absorbent core comprises at least 60% by weight of SAP by total weight of the core.

14. The absorbent core of claim 1, comprising a first high loft central layer and a second high loft central layer between the top cover layer and the bottom cover layer, wherein at least one of the first central layer and the second central layer is a central layer having SAP1 and SAP2 partially distributed within.

15. An absorbent article comprising a liquid permeable topsheet, a liquid impermeable backsheet and an absorbent core of claim 1, wherein the top cover layer of the absorbent core is oriented towards the topsheet of the article.

16. A package comprising a plurality of absorbent articles according to claim 15.

17. A method for making an absorbent core according to claim 1, the method comprising:
providing a high loft central layer, a liquid-permeable top cover layer, and a bottom cover layer;
depositing a layer of the first superabsorbent particles, SAP1, on a first side of the high loft central layer such that the SAP1 particles are substantially uniformly blended across the thickness of the high loft central layer and such that the SAP1 particles are partially distributed in the z-distribution pattern comprising two or more peaks of density separated by at least one buffer zone in the vertical direction within the high loft central nonwoven;
covering the first side of the central layer with the liquid-permeable top cover layer;
depositing a layer of the second superabsorbent particles, SAP2, on the second side of the high loft central layer such that the SAP2 particles are substantially uniformly blended across the thickness of the high loft central layer, and the SAP2 particles are partially distributed in the z-distribution pattern comprising two or more peaks of density separated by at least one buffer zone in the vertical direction within the high loft central nonwoven; and
covering the second side of the central layer with the bottom cover layer.

18. The method according to claim 17, wherein the initial density of the high loft central layer is in the range of from about 0.05 g/cm3 to about 0.15 g/cm3 measured at 4.14 kPa (0.6 psi) and wherein the initial thickness of the central layer is of more than about 0.30 mm measured at 4.14 kPa (0.6 psi).

19. The absorbent core of claim 1, wherein the high loft central layer is free of free cellulose fibers.

20. The absorbent core of claim 1, wherein the absorbent core is free of free cellulose fibers.

* * * * *